(12) United States Patent
Malmgren et al.

(10) Patent No.: US 6,774,151 B2
(45) Date of Patent: Aug. 10, 2004

(54) METHOD OF PRODUCING AN ABSORBENT FOAM MATERIAL

(75) Inventors: Kent Malmgren, Harmonigatan (SE); Bengt Widberg, Bågevägen (SE)

(73) Assignee: SCA Hygiene Products AB, Göteborg (SE)

( * ) Notice: Subject to any disclaimer, the term of this patent is extended or adjusted under 35 U.S.C. 154(b) by 185 days.

(21) Appl. No.: 10/061,109

(22) Filed: Feb. 1, 2002

(65) Prior Publication Data

US 2002/0143310 A1 Oct. 3, 2002

Related U.S. Application Data

(63) Continuation of application No. PCT/SE00/01612, filed on Aug. 23, 2000.

(30) Foreign Application Priority Data

Aug. 30, 1999 (SE) ................................................ 9903071

(51) Int. Cl.[7] .......................... C08J 9/28; A01H 25/02; A61K 9/34; A61F 13/15
(52) U.S. Cl. .......................... 521/64; 521/84.1; 424/43; 424/485; 424/488; 424/499; 424/500; 604/358; 604/369
(58) Field of Search .................... 521/64, 84.1; 424/43; 424/485, 488, 499, 500; 604/358, 369

(56) References Cited

U.S. PATENT DOCUMENTS

| | | |
|---|---|---|
| 3,512,450 A | 5/1970 | Portal |
| 5,718,916 A | 2/1998 | Scherr |
| 6,608,117 B1 * | 8/2003 | Gvozdic |

FOREIGN PATENT DOCUMENTS

| | | |
|---|---|---|
| EP | 0 293 208 A1 | 11/1988 |
| EP | 0 598 833 B1 | 6/1994 |
| EP | 0 747 420 A1 | 12/1996 |
| EP | 0 804 913 A1 | 11/1997 |
| WO | 94/00512 | 1/1994 |
| WO | 95/31500 | 11/1995 |
| WO | 98/55540 | 12/1998 |

* cited by examiner

Primary Examiner—Morton Foelak
(74) Attorney, Agent, or Firm—Burns, Doane, Swecker & Mathis, L.L.P.

(57) ABSTRACT

A method of producing a porous, liquid absorbent, open-cell polymeric foam material having properties which makes it suitable for use as an absorbent structure in absorbent articles such as diapers, pant diapers, sanitary napkins, incontinence guards, wound dressings, bed protections etc, comprising dissolving a polymer in a solvent, adding a surfactant and causing foaming, after which the polymer is crosslinked in the foamed mixture by means of a crosslinking agent. The temperature of the foam thus formed is lowered to a temperature below the freezing point of the solvent and the crosslinking reaction is continued during the freezing step, and after the main part of the solvent is removed from the formed foam material.

7 Claims, 3 Drawing Sheets

METHOD OF PRODUCING AN ABSORBENT FOAM MATERIAL

This application is a continuation of International Application No. PCT/SE00/01612 filed on 23 Aug. 2000, which International Application was published by the International Bureau in English on 08 Mar. 2001.

TECHNICAL FIELD

The present invention refers to a method of producing a liquid absorbent open-cell polymeric foam material having properties which makes it suitable for use as an absorbent structure in absorbent articles such as diapers, pant diapers, sanitary napkins, incontinence guards, wound dressings, bed protections etc, said method comprising dissolving a polymer in a solvent, adding a surfactant and causing foaming, after which the polymer is crosslinked in the foamed mixture by means of a crosslinking agent.

BACKGROUND OF THE INVENTION

Absorbent articles of the above mentioned kind are intended to be used for absorption of body liquids such as urine and blood. They usually comprise a liquid pervious topsheet, which during use is intended to be facing the wearer's body, e g a nonwoven material of spunbond type, a meltblown material, a carded bonded wadding etc. They further have a liquid impervious backsheet, e g a plastic film, a plastic coated nonwoven or a hydrophobic nonwoven, and an absorbent structure arranged between the liquid pervious topsheet material and the liquid impervious backsheet. This absorbent structure may be constructed by several layers such as a liquid acquisition layer, storage layer and distribution layer in order to fulfil the functions which are desired in an absorbent structure: capacity to quickly receive liquid, distribute it in the structure and store it.

As a liquid acquisition layer there is usually used a porous material having a high momentaneous liquid receiving capacity. Such materials are open, bulky structures with large capillaries, for example cellulosic fluff pulp of thermomechanic or chemothermomechanic (CTMP) type, chemically stiffened cellulosic fibers, synthetic fiber structures of different types and porous foam materials etc.

As a storage layer there is usually used cellulosic fluff pulp mixed with so called superabsorbents, which are polymers with the ability to absorb several times their own weight (10 times or more) of body fluids. It is also possible to use an absorbent foam material as a storage layer. As a distribution layer there can be used cellulosic fluff pulp, tissue layers, foam, synthetic fibers and the like having high liquid distribution capacity.

It is also possible to combine two or more of the functions acquisition, storage and distribution in one and the same layer.

It is previously known through U.S. Pat. No. 3,512,450, EP-A-0 293 208 and EP-A-0 804 913 to use a compressed foam material of regenerated cellulose, e g viscose, as an absorbent structure in an absorbent article of the above mentioned kind, e g a sanitary napkin. The article may then be made very thin and still have a high absorption capacity. The compressed viscose foam expands quickly i the z-direction when liquid is absorbed by the material when wetted.

The production of absorbent foams based on polysaccharides by foaming an aqueous solution of a polysaccharide and a surfactant by mechanical agitation or gas supply, and then stabilize the foam by crosslinking with a covalent or ionic crosslinking agent, is previously known through WO 94/00512 and EP-A-0 747 420. The foam may for example be used as a carrier material in medical applications and in wound dressings. Nothing is mentioned about specific absorbent properties.

WO 95/31500 describes the production of absorbent porous foams having a mean pore size below 100 $\mu$m. The foam is produced by dissolving a polymer and a crosslinking agent in a solvent, after which a phase separation takes place in a polymer-concentrated phase and a polymer-diluted phase, and where crosslinking occurs in the concentrated phase. The produced foam is said to have an absorbent capacity of at least 2 and preferably at least 10 g/g and be suited as an absorption material in for example diapers.

In EP-B-0 598 833 there is disclosed a foam material intended as an absorbent structure of the above stated kind. The foam material has a specified pore volume, specific surface area and ability to resume its volume after compression. The foam is a so called "HIPE"-foam (high internal phase emulsion), which means that the foam is produced by polymerization of a water-in-oil emulsion. The solid phase in the foam creates a capillary system, which receives, distributes and stores liquid. There is no indication about the liquid storage capacity of the foam measured by CRC (centrifuge retention capacity), which is a measure of the capacity of the foam to firmly bind liquid, so called gel liquid, in its solid phase by swelling the cell walls.

OBJECT AND MOST IMPORTANT FEATURES OF THE INVENTION

The object of the invention is to provide a method of producing a foam material suited to be used as an absorbent structure in an absorbent article of the above mentioned kind and which has multifunctional properties in such a way, that it at the same time fulfils the function of a liquid acquisition layer, a storage layer and a distribution layer, namely the capacity to quickly receive liquid, distribute it in the structure and store it. The method should further be adapted for a large number of polymeric materials, including polymers based on renewable raw materials such as polysaccharides and polypeptides.

This has according to the invention been provided by dissolving a polymer in a solvent, adding a surfactant and cause foaming, adding a crosslinking agent to the foamed mixture, after which the temperature of the foam thus formed is lowered below the freezing point of the solvent and letting the crosslinking reaction continue during the freezing step, and that after that the main part of the solvent is removed from the foam material.

By the freezing step the foam is given unique properties concerning liquid absorption and obtains a firm porous structure at the same time as it is soft and flexible. It is assumed that the freezing step influences the crosslinking in a positive way, which in turn influences the structure and shape stability of the foam. The foam may also be compressed to a high density and then be able to swell and expand upon contact with liquid.

The polymer is preferably a polysaccharide or a polypeptide.

The solvent is preferably water.

According to one embodiment fibers can be added to the polymer solution, preferably hydrophilic fibers such as for example cellulosic fibers. It can sometimes be desired to produce absorbent products having an anatomic three-dimensional shape, which with the foam according to the present invention can be provided by after foaming and before freezing applying the foam in a mould, and keeping the foam in the mould during the freezing step.

DESCRIPTION OF DRAWINGS

The invention will in the following be closer described with reference to the embodiments shown in the accompanying drawings.

DESCRIPTION OF EMBODIMENTS

Figure 1:
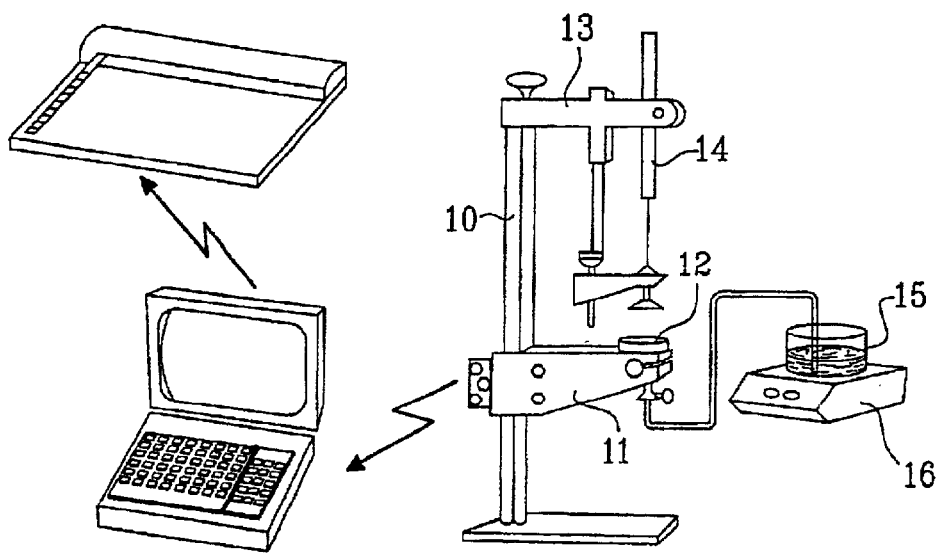
FIG. 1 shows a measuring apparatus for measuring the absorption rate.

The invention refers to liquid absorbent foam materials with specific well-defined properties which make them suited to use as absorbents for body liquids, such as urine, blood and wound discharges. The foam material may thus be used as the entire or part of the absorbent structure in absorbent articles such as diapers, pant diapers, sanitary napkins, incontinence guards, wound dressings, bed protections etc.

A foam is built of a continuous three-dimensional network or cellular structure of a solid or liquid phase, which surrounds a gaseous phase dispersed therein. In a polymeric foam the solid phase is a polymeric material, which forms the cell walls in the continuous cellular phase. The cells may have different shape, size and topography and be open or closed. In this case the cell structure is open which means that the cells communicate with each other. The term foam as defined according to the present invention also encompasses such materials where fibers of different types are integrated in the cell structure.

Polymeric foams are produced from the polymer itself or from the monomers which are to be polymerized possibly with the addition of crosslinking agents, foam forming additives and/or additives for cell stabilization. There are different methods for foam generation such as mechanical agitation, air injection, heating, gas generation, evaporation, enzymatic decomposition and phase separation techniques.

Several open-cell polymeric foam material function well as liquid absorbents and can be heavily compressed, and then swell in contact with liquid, at which the liquid is absorbed into the cell structure of the foam.

According to the invention such open-cell polymeric foam materials are preferred which have multifunctional absorption properties with respect to liquid acquisition capacity, distribution capacity and storage capacity. The material should thus be able to simultaneously fulfil the functions of a liquid acquisition layer, distribution layer and storage layer.

According to a preferred embodiment of the invention the foam material according to the invention constitutes the sole component of the absorbent structure of the absorbent article. It can also replace the liquid pervious topsheet which normally covers the absorbent structure and which is intended to be located closest to the skin of the wearer.

In order that an absorption material will have the preferred multifunctional properties it is required that it has a relatively broad pore volume distribution, i e it should in its capillary structure contain pores with a varying mean pore size within the interval 0–500 $\mu$m. The pore volume distribution (PVD) is determined by means of a PVD apparatus manufactured by Textile Research Institute, Princeton, USA. The function of the PVD apparatus is described in detail in Miller, B. and Tyomkin, L. Textile Reseach Journal 56(1986) 35.

In order that a foam will have the multifunctional absorption properties aimed at it is desirable to have a distribution of its absorption capacity in the form of capillary liquid and gel liquid. Gel liquid refers to liquid held in pores smaller than 3 $\mu$m and capillary liquid refers to loosely bound liquid in pores larger than 3 $\mu$m and up to 500 $\mu$m. Gel liquid is the liquid that is held most firmly in the structure. It is desirable that the gel liquid absorption, determined as the total amount of liquid in pores below 3 $\mu$m according to PVD measurements, is at least 4 g/g and preferably at least 5 g/g of synthetic urine. The capillary liquid absorption determined as the total amount of liquid in pores between 3–100 $\mu$m according to PVD measurements, should be at least 8 ml/g, preferably at least 10 ml/g.

As stated above it is preferred that the foam material according to the invention has defined values of liquid acquisition, distribution and storage capacity respectively. Thus it should preferably have an absorption rate at wetting of at least 0.4 ml/s for a round sample having the diameter 50 mm, said absorption rate being determined by the below defined measuring method for liquid acquisition capacity. Preferably its absorption rate should be at least 0.5 ml/s. It is further preferred that the liquid distribution capacity at an inclination of 30° is at least 15 g/g and preferably at least 16 g/g, measured according to the below defined measuring method for distribution capacity. It is further preferred that the foam has a storage capacity of at least 9% and preferably at least 11% measured through the below defined measuring method for storage capacity (CRC=centrifuge retention capacity).

Test Liquid

In all cases the test liquid was synthetic urine according to the following recipe: 0.66 g/l $MgSO_4$, 4.47 g/l KCl, 7.60 g/l NaCl, 18.00 g/l $NH_2CONH_2$ (urea), 3.54 g/l $KH_2PO_4$, 0.754 g/l $Na_2HPO_4$, 1 ml/l of a 0.1% solution of Triton X-100, which is a surfactant sold by Aldrich. The substances were dissolved in deionized water.

Absorption Rate

The liquid acquisition capacity was measured according to the below described measuring apparatus for determining the absorption rate of a sample. The measuring apparatus is shown in FIG. 1 and comprises a stand 10 with a holder 11 for a glass filter plate (porosity 1, supplier Werner-Glas AB, Stockholm) and holder 3 for a thickness gauge 14. The glass filter plate 12 is provided with a liquid (synthetic urine) from a glass bowl 15 placed on a scale 16. The holder 11 for the glass filter plate 12 is vertically adjustable, which makes the hydrostatic pressure adjustable. The liquid level in the bowl 15 should be only 2 cm below the level of the glass filter plate 12. With this hydrostatic pressure pores up to 250 $\mu$m will be filled with liquid if the contact angle between the sample, which is placed on the glass filter plate 12, and the liquid is supposed to be 70°. The measuring signals from the scale and the thickness gauge are transmitted to a computer with 15 datum/s at measuring periods of up to 60 seconds. At longer measuring periods the signal speed becomes lower. The measurement is started automatically by means of a contact when the sample reaches the glass filter plate 12. The measurement result is printed by a printer as a function of time.

Round samples with the diameter 50 mm were punched out from the foam material. The foam material was conditioned before testing at least for 4 hours at 50% relative humidity and a temperature of 23° C. The glass filter plate 12 should be saturated with test liquid (synthetic urine) when the measurement is started. The samples are attached against the glass filter plate by a pair of minimal pieces of double-sided adhesive tape. The samples were loaded during the measurement with a pressure of 0.57 kPa.

The absorption progress can be divided into three phases:

1) "The initial phase". The sample absorbs liquid unevenly on the surface that is in contact with the glass filter plate. First when the entire surface is covered with liquid the next phase "steady state" begins.

2) "Steady state". Here liquid spreads like a front up through the sample, i e absorption takes place only in the z-direction. The absorbed liquid amount increases linearly with time.

3) "The finishing phase". Here the liquid has reached the top of the sample and begins to spread over the entire upper limiting surface. When the entire upper surface is covered with liquid the absorption stops.

Figure 2:
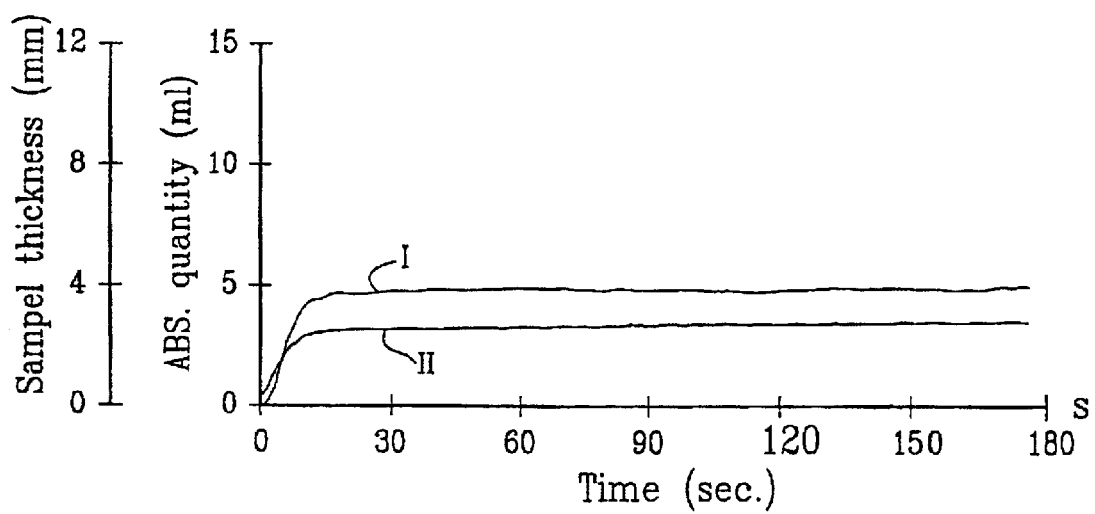
FIG. 2 shows an example of an absorption graph measured with the measuring apparatus according to FIG. 1.

One example of an absorption graph is shown in FIG. 2, at which the graph I shows the absorption progress and graph II shows the change of thickness of the sample during the absorption.

The absorption rate in "steady state" is calculated from the linear part of the absorption graph, where the absorbed liquid amount increases linearly with time, i e as the coefficient of direction and is expressed in ml/s.

Liquid Distribution Capacity

In this method the amount of liquid is measured which is absorbed and distributed during 60 minutes by the material, which is placed with an inclination of 30°. Samples with the dimension 1.5×28 cm were punched out. The samples were conditioned in 50% relative humidity (RH) and 23° C. for 24 h±2 h. The samples can then be stored dark in plastic bags for up to 14 days. The testings were performed in climate room 50% RH and 23° C.

Figure 3:
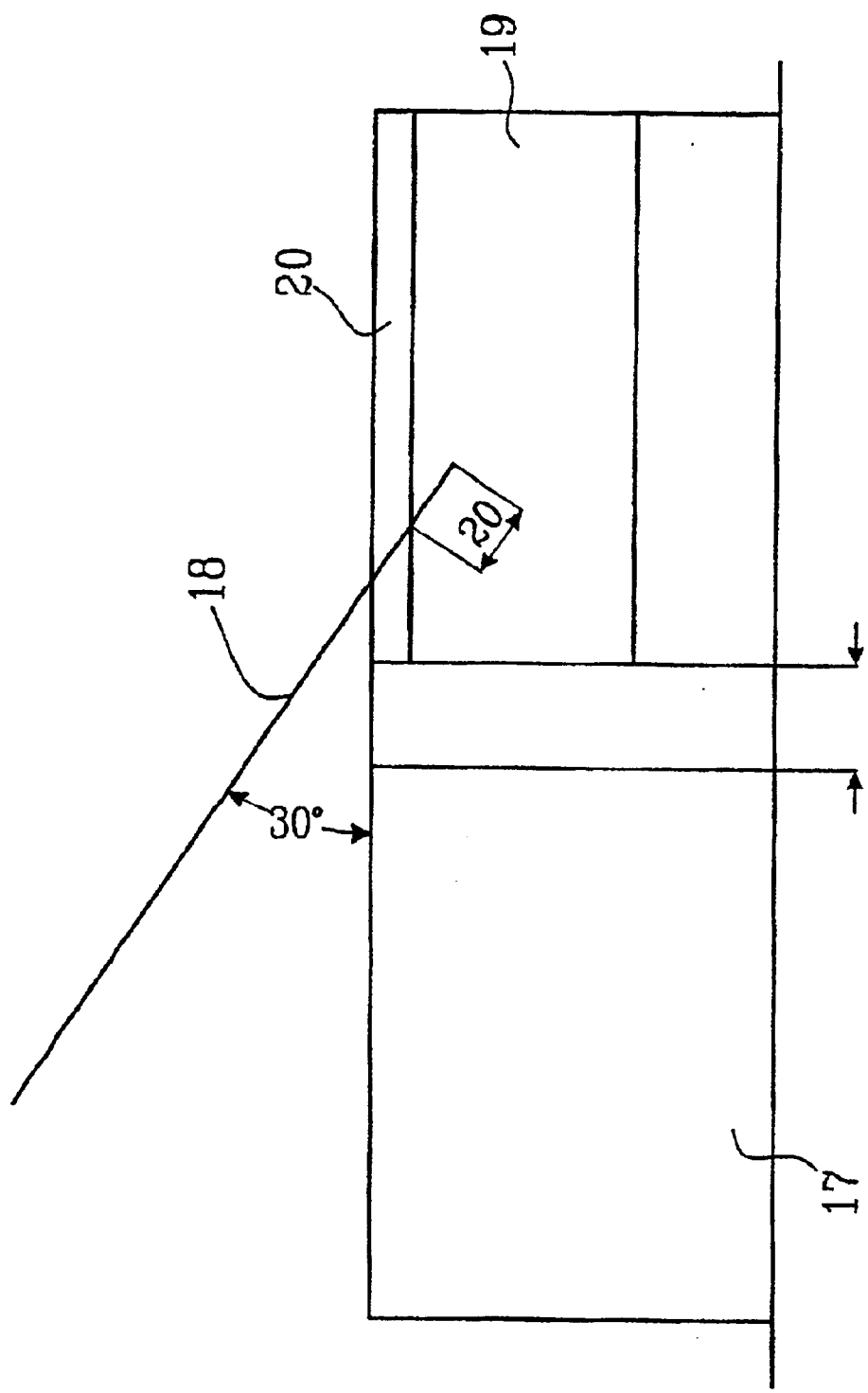
FIG. 3 shows a measuring apparatus for determining the liquid distribution rate.

A measuring apparatus which is schematically shown in FIG. 3 were used at the testings. The measuring apparatus comprises a scale 17, a plexi glass plate 18 and a liquid container 19, in which the liquid surface is indicated with 20. The liquid container 19 is placed adjacent the scale 17, at which it is important that both take a horizontal position. The plexi glass plate 18 is placed on the scale with an inclination of 30° with respect to the horizontal plane without touching the liquid container 19. Test liquid is poured into the liquid container 19, so that 20 mm of plexi glass plate is below the liquid surface 20. The sample is weighed with an accuracy of measurement of 0.1 g and is placed on the plexi glass plate 18 without the sample touching the liquid. The scale is then calibrated. The sample is then moved along the plexi glass plate 18 so that 20 mm of the sample will be below the liquid surface, i e the end of the sample will be 10 mm below the liquid surface as seen in the vertical direction, after which the sample is fixed in this position with a clamp. After exactly 60 minutes the measurement is interrupted and the sample is weighed again. It is also measured how long distance of the sample has been wetted on the underside and on the upperside respectively. The liquid distribution capacity is calculated as: $m_2/m_1$ (g/g) where $m_2$ is the weight of the sample after the measurement, and
$m_1$ is the dry weight of the sample before the measurement.

Storage Capacity

The storage capacity of the foam was measured according to the so called CRC method (centrifuge retention capacity). This involves that the sample is allowed to absorb liquid freely until saturated and is weighed, after which weight $_{(saturated)}$ is obtained. Then the sample is centrifugated during 10 minutes at 1500 rpm, which approximately corresponds to a load of 300 g. The sample is weighed after centrifugation, at which weight$_{(centrifugated)}$ is obtained. By then calculating the quotient between weight$_{(centrifugated)}$ and weight$_{(saturated)}$ and multiply with 100 the storage capacity of the sample in percent is obtained.

Method for Producing a Foam Material According to the Invention

Below there is disclosed a method for producing a foam material according to the invention. As a first step of the foam production a polymer solution is prepared by dissolving a polymer in a solvent, preferably water. The polymer is preferably a polymer containing functional crosslinkable groups, e g carboxy-, hydroxy- or amino groups, e g a polysaccharide or polypeptide. Examples of useful polysaccharides are carboxy methyl cellulose (CMC), carboxy ethyl cellulose, starch derivatives etc.

In the case of CMC a suitable concentration of the polymer solution is 0.5–10% by weight, at which water is used as solvent. This concentration must however be adapted to the polymer used.

Then there is added a suitable surfactant and by mechanical agitation a foam is created. Alternatively air injection is used for creating the foam. Possibly one or more different surfactants are added to the solution to control the properties of the foam such as porosity and stability.

In case it is desired that the foam should contain fibers these are preferably added in connection with the foaming of the polymer solution. The fibers are mainly used for improving the mechanical properties of the produced foam. On one hand the ability of the foam to withstand both tensile and shearing forces will increase and on the other hand it will be more compressible, in e it can be compressed to high densities and yet expand at wetting. The latter of course improves the capillary absorption capacity of the foam after compression and since often thinness of absorbent articles are strived for fiber addition can give special advantages. Besides fiber addition can improve the liquid distribution properties of the foam.

Suitable fibers are different types of hydrophilic natural or synthetic fibers. Preferably pulp fibers are used, especially chemical pulp.

When using CMC as the polymeric substance an alkaline compound is preferably added, e g NaOH, for activating the CMC to react with the crosslinking agent. The amount of the alkali relative to the amount of crosslinking agent effects the reaction speed, which increases at an increase of the alkali amount. The order of addition between polysaccharide (CMC), surfactant, possible fibers and alkali may be varied and it is also possible to mix all components at the same time. It is however important that they are well mixed and that air or possibly some other gas can be mixed into the material so that a porous foam is formed. The method of mixing and foam formation can be mechanical agitation, gas injection or extrusion under press reduction.

In the next step the crosslinking agent should be added. It is here desired to have a homogeneous distribution thereof in the material before the crosslinking reaction starts. It can therefore be advantageous to work at low temperatures, since the temperature is important for the reaction speed. The foam may for example be cooled to a temperature close to 0° C. before the crosslinking agent is added. It can however be possible to achieve good results also with room tempered foams especially if the alkali addition is reduced.

Suitable crosslinking agents are cyanuric chloride, formaldehyde, dimethyl urea, diepoxides, glutaraldehyde, glyoxal, divinyl sulphone, epichlorhydrine etc. The crosslinking agent is added under strong mechanical stirring in order to obtain a good mixing. The crosslinking agent can possibly be dissolved in a small amount of solvent in order to enhance the distribution of the crosslinking agent in the foam.

After this step the viscous but liquid foam is shaped by placing it in a suitable mould. After then the foam is frozen. After thawing of the frozen foam this has transferred from a liquid condition to a solid, porous and liquid absorbent condition with unique properties with respect to liquid acquisition, distribution and storage capacity.

According to a theory to which however the invention is not bound the following things happen during the freezing step:

a) Water concentrates in the form of ice crystals, which break up the foam structure and makes it porous after removal of the water. This effects the absorption capacity of the material in a favourable way.

b) As a result of the separation of water in connection with the formation of ice crystals there will be a concentration of polymer between the ice crystals. This makes the polymer chains coming closer to each other, at which the reduced distance between the polymer chains increases the opportunities to crosslinking reactions.

c) The water separation also makes that the alkali content close to the polymer chains increases, which make them more disposed to react with the crosslinking agent.

After freezing and thawing the foam is washed in order to remove undesired chemicals and secure so that the material is innoxious from product safety point of views. This step is preferably combined with deswelling of the material and removal of water. The foam is herewith washed with a suitable solvent which can deswell the foam and dissolve the water. Examples of such solvents are ethanol, acetone and methanol. Finally the material is dried by evaporating the liquid.

The foam thus prepared has a solid porous structure and is also soft and flexible. It has excellent absorption properties which makes it suitable to use in different types of absorbent articles mentioned above. It may also be shaped into a desired three-dimensional shape, which is determined by the shape of the mould in which the foam is applied during the freezing step. The foam can be compressed to a high density, and then swell again while absorbing liquid. The latter property is very interesting if the foam is to be used in thin products.

Examples 1–3 below describes production of some different types of foam materials according to the invention and table 1 describes the absorption properties of the materials in comparison to some reference materials.

| Raw materials used at the foam production | |
|---|---|
| Cekol 50000 | Carboxy methyl cellulose from Metsä Chemicals. Highly viscous quality with a substitution degree of about 0.8. |
| Celpol RX | Carboxy methyl cellulose from Metsä Chemicals. Highly viscous quality with a substitution degree of about 1.2. |
| Softwood sulphate | SCA Graphic Paper, Sundsvall, Sweden. |
| Cyanuric chloride | Merck-Schuchardt. Degree of purity: For synthesis. |
| Berol 048 | Nonionic surfactant from Akzo |
| Berocell 451 | Anionic surfactant from Akzo Nobel. |
| Sodium hydroxide | EKA Nobel. Degree of purity: min 97%. |
| Methyl ketone | E. Merck. Degree of purity: For synthesis. |

EXAMPLE 1

A liquid foam was produced by vigorous mixing with an electric beater of the following mixture: 220 g of a 3% solution of Celpol RX in water, 2.82 g bleached softwood sulphate pulp, 80 g water, 0.13 g NaOH, 1.0 g Berocell 451 and 1.0 g Berol 048. The foam was cooled to a temperature of about 2° C. after which 0.264 g of cyanuric chloride dissolved in 5 g methyl ethyl ketone was added to the foam mixture.

After vigorous stirring for 3 minutes the foam was spread to a layer with an area of about 1600 cm$^2$ on a plane plastic surface (PVC) and was frozen at about –18° C. After about 20 hours the frozen foam was released from the plastic surface and was thawed in a water bath. A water swollen but insoluble foam was obtained. It was washed and deswollen by leaching in ethanol and was dried at room temperature. After drying the solid foam was compressed by pressing it between rolls in a laboratory calendar of the mark Kusters to a bulk of about 3.0 cm$^3$/g.

EXAMPLE 2

Two liquid foams were prepared by vigorous mixing of the two following mixtures: 1.110 g of a 3% solution of Celpol RX in water, 1.41 g bleached softwood sulphate pulp, 40 g water, 0.057 g NaOH, 0.5 g Berocell 451 and 0.5 g Berol 048.

2.110 g of a 3% solution of Cekol 50000 in water, 1.41 g bleached softwood sulphate pulp, 40 g water, 0.091 g NaOH, 0.5 g Berocell 451 and 0.5 g Berol 048.

Both foams were cooled to a temperature of about 2° C. after which 0.264 g cyanuric chloride dissolved in 5 g methyl ethyl ketone was added to the first mentioned foam mixture. After vigorous stirring during about 3 minutes the foams were mixed carefully for about 2 minutes.

After that the foam was spread out to a layer with an area of about 1600 cm$^2$ on a plane plastic surface (PVC) and was frozen at about –18° C. After about 20 hours the frozen foam was released from the plastic surface and was thawed in a water bath. A water swollen but insoluble foam was obtained. This was washed and deswollen by leaching in ethanol and was dried at room temperature. After drying the solid foam was compressed by pressing it between rolls to a bulk of about 3.1 cm$^3$/g.

EXAMPLE 3

Two liquid foams were manufactured by vigorous mixing of the following mixtures: 1.110 g of a 3% solution of Celpol RX in water, 1.41 g bleached softwood sulphate pulp, 40 g water, 0.057 g NaOH, 0.5 g Berocell 451 and 0.5 g Berol 048. 2.110 g of a 3% solution of Cekol 50000 in water, 1.41 g bleached softwood sulphate pulp, 40 g water, 0.091 g NaOH, 0.5 g Berocell 451 and 0.5 g Berol 048. Both foams were cooled to a temperature of about 2° C. after which 0.264 g cyanuric chloride dissolved in 10 g methyl ethyl ketone was added to the first mentioned foam mixture. After vigorous mixing for about 3 minutes the foams were mixed carefully during about 2 minutes.

After that the foam was spread out to a layer with an area of about 1600 cm² on a plane plastic surface (PVC) and was frozen at about −18° C. After about 20 hours the frozen foam was released from the plastic surface and was thawed in a water bath. A water swollen but insoluble foam was obtained. This was washed and deswollen by leaching in ethanol and was dried at room temperature. After drying the solid foam was compressed by pressing it between rolls to a bulk of about 2.4 cm³/g.

Measurement Results of Absorption Properties

In Table 1 below the measurement results are shown concerning absorption rate, liquid distribution capacity and liquid storage capacity, which were measured for the different test foams 1, 2 and 3 according to Examples 1, 2 and 3 above as compared to some reference materials in the form of a pair of commercially available foam materials, viz. Vileda from Freudenberg Household Products AB and Vibrofoam from Nova-Sorb Ltd.

TABLE 1

| Material | Abs. Rate (ml/s) | Distribution capacity (g/g) | Storage capacity (%) |
| --- | --- | --- | --- |
| Test foam 1 | 0.48 | 16.1 | 30 |
| Test foam 2 | 0.53 | 18.8 | 26 |
| Test foam 3 | 0.63 | 24.2 | 12 |
| Vileda | 2.1 | 4.5 | 5.5 |
| Vibrofoam | 0.015 | — | 53 |

From these results it is seen that the foam materials according to the invention have high absorption rate, liquid distribution capacity as well as storage capacity, while the reference materials either had high absorption rate (Vileda) or a high storage capacity (Vibrofoam).

Pore Volume Distribution Measurements (PVD)

Figure 4A:
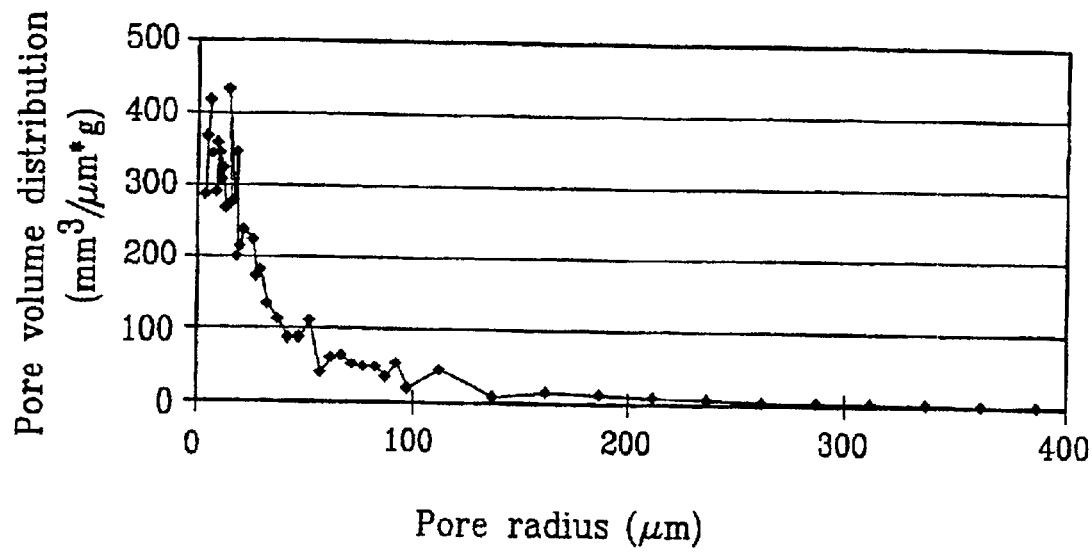
FIGS. 4a and b shows the pore volume distribution for a foam material according to the invention.
Figure 4B:
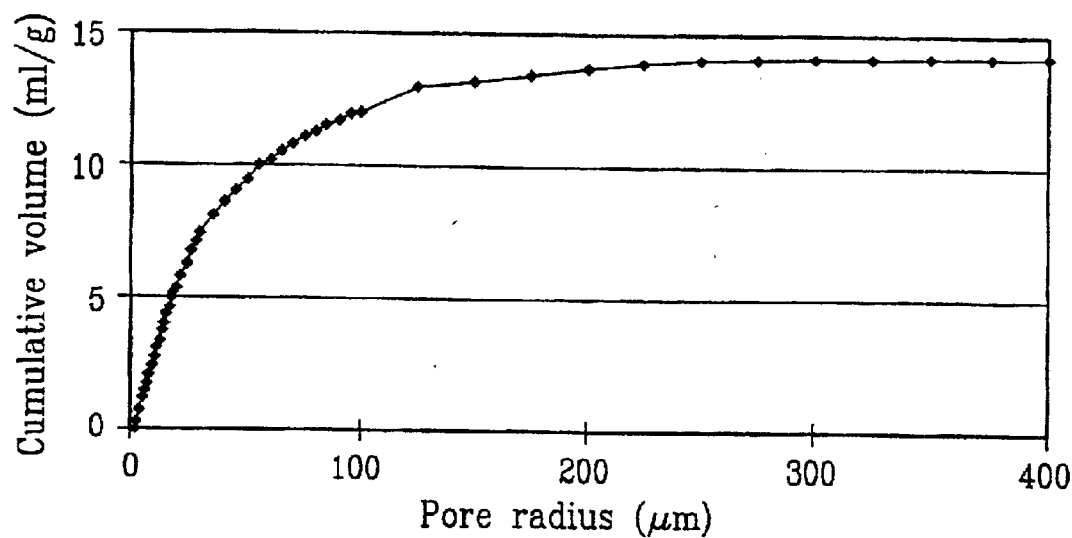

The pore volume distribution of the foam materials according to example 3 was determined by means of a PVD apparatus from Textile Research Institute, Princeton. USA. The material was swollen in synthetic urine during about 1 hour and its pore volume distribution was then determined. The material was tested with a mechanical load of 0.57 kPa. In FIG. 4a there is shown the pore volume distribution and in FIG. 4b there is shown the cumulative volume, in e liquid in ml/g dry sample, in pores between 3 μm and the value noted on the x-axis.

In pore volume measurements liquid held in pores below 3 μm can not be removed and the distribution graph thus only describes the pore volume distribution in pores with the size 3 μm and larger. It is therefore possible by weighing the sample after finished measurement to determine the total liquid amount in pores below 3 μm. This liquid concentration in g/g dry material is defined as gel liquid and was at this measurement 5.62 g/g.

What is claimed is:

1. A method of producing a porous, liquid absorbent, open-cell polymeric foam material for use as an absorbent structure in an absorbent article, the method comprising dissolving a polymer in a solvent, adding a surfactant and causing foaming, after which the polymer is crosslinked in the foamed mixture by means of a crosslinking agent, lowering the temperature of the foam thus formed to a temperature below the freezing point of the solvent and continuing the crosslinking reaction during the freezing step, and after that removing the main parts of the solvent from the formed foam material.

2. A method as claimed in claim 1, wherein the polymer is polysaccharide or a polypeptide.

3. A method as claimed in claim 1, herein the solvent is water.

4. A method as claimed in claim 1, wherein fibers are added to polymer solution.

5. A method as claimed in claim 4, wherein the fibers are hydrophilic and preferably are cellulose fibers.

6. A method as claimed in claim 1, wherein after foam formation and before freezing the foam is applied in a mold in which it remains during the freezing.

7. The method as claimed in claim 1, wherein the absorbent article is a diaper, pant diaper, sanitary napkin, incontinence guard, wound dressing, or a bed protector.

* * * * *